(12) United States Patent
Chin et al.

(10) Patent No.: US 9,498,560 B2
(45) Date of Patent: Nov. 22, 2016

(54) INTERSPINOUS SPACER IMPLANT

(75) Inventors: Kingsley R. Chin, Wilton Manors, FL (US); Matthew Ibarra, Lakewood, CA (US); Craig Henshaw, Charlestown, MA (US); Michael Drnek, Boston, MA (US); Charles Sears, Boxford, MA (US)

(73) Assignee: SPINEFRONTIER, INC, Malden, MA (US)

( * ) Notice: Subject to any disclaimer, the term of this patent is extended or adjusted under 35 U.S.C. 154(b) by 515 days.

(21) Appl. No.: 13/411,478

(22) Filed: Mar. 2, 2012

(65) Prior Publication Data

US 2012/0226314 A1 Sep. 6, 2012

Related U.S. Application Data

(63) Continuation-in-part of application No. 13/182,525, filed on Jul. 14, 2011, now abandoned.

(60) Provisional application No. 61/449,274, filed on Mar. 4, 2011.

(51) Int. Cl.
*A61B 17/70* (2006.01)
*A61L 27/42* (2006.01)
(Continued)

(52) U.S. Cl.
CPC .......... *A61L 27/425* (2013.01); *A61B 17/1671* (2013.01); *A61B 17/7062* (2013.01); *A61B 17/7065* (2013.01); *A61B 17/7067* (2013.01); *A61B 17/7068* (2013.01); *A61B 17/1659* (2013.01); *A61B 17/32053* (2013.01); *A61B 2017/0256* (2013.01); *A61B 2090/061* (2016.02); *A61F 2/3094* (2013.01); *A61F 2/30965* (2013.01); *A61F 2/4611* (2013.01); *A61F 2002/2817* (2013.01); *A61F 2002/2835* (2013.01); *A61F 2002/3082* (2013.01); *A61F 2002/3085* (2013.01); *A61F 2002/30777* (2013.01); *A61F 2002/30785* (2013.01); *A61F 2002/30841* (2013.01); *A61F 2002/30909* (2013.01); *A61F 2002/448* (2013.01); *A61F 2002/4475* (2013.01); *A61F 2310/00017* (2013.01); *A61F 2310/00023* (2013.01); *A61F 2310/00029* (2013.01); *A61F 2310/00293* (2013.01); *A61F 2310/00329* (2013.01); *A61F 2310/00365* (2013.01)

(58) Field of Classification Search
CPC ................... A61B 17/17065; A61B 17/7067; A61B 17/7068
USPC .................................................. 606/248–249
See application file for complete search history.

(56) References Cited

U.S. PATENT DOCUMENTS 7,749,252 B2 7/2010 Zucherman et al.
7,771,456 B2 8/2010 Hartmann
(Continued)

*Primary Examiner* — Nicholas Woodall
(74) *Attorney, Agent, or Firm* — AKC Patents LLC; Aliki K. Collins

(57) ABSTRACT

An improved spinous process fixation implant assembly 50 includes a spinous process fixation implant 100 and an interspinous spacer implant 200. The spinous process fixation implant 100 includes elongated first and second components 110, 120, that are arranged opposite and parallel to each other. First and second spinous processes 90a, 90b of first and second adjacent vertebrae 80a, 80b are clamped between the first and second components 110, 120, respectively, and are separated by the interspinous spacer implant 200. The interspinous spacer implant 200 may be inserted between the spinous processes of adjacent vertebrae from two different directions.

6 Claims, 12 Drawing Sheets

(51) Int. Cl.
   *A61F 2/30*     (2006.01)
   *A61F 2/46*     (2006.01)
   *A61F 2/28*     (2006.01)
   *A61F 2/44*     (2006.01)
   *A61B 17/16*    (2006.01)
   *A61B 17/02*    (2006.01)
   *A61B 17/3205*  (2006.01)

(56) References Cited

U.S. PATENT DOCUMENTS

| | | |
|---|---|---|
| 7,828,822 B2 | 11/2010 | Zucherman et al. |
| 8,048,117 B2 | 11/2011 | Zucherman et al. |
| 2004/0162617 A1 | 8/2004 | Zucherman et al. |
| 2006/0241610 A1* | 10/2006 | Lim et al. ............. 606/69 |
| 2006/0264939 A1 | 11/2006 | Zucherman et al. |
| 2007/0016303 A1 | 1/2007 | Jackson |
| 2007/0093825 A1* | 4/2007 | Ferree et al. ............ 606/61 |
| 2008/0033552 A1 | 2/2008 | Lee et al. |
| 2009/0138046 A1 | 5/2009 | Altarac et al. |
| 2009/0234389 A1 | 9/2009 | Chuang et al. |
| 2009/0306715 A1 | 12/2009 | Jackson et al. |
| 2010/0106191 A1 | 4/2010 | Yue et al. |
| 2010/0174316 A1 | 7/2010 | Zucherman et al. |
| 2010/0222817 A1 | 9/2010 | Perez-Cruet et al. |
| 2011/0054533 A1 | 3/2011 | Binder et al. |
| 2011/0307010 A1 | 12/2011 | Pradhan |

* cited by examiner

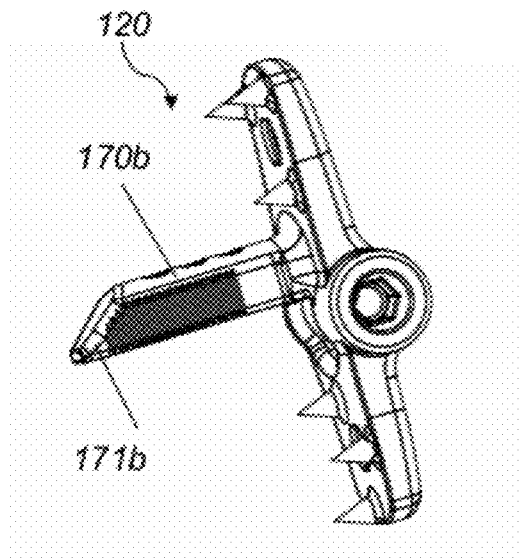 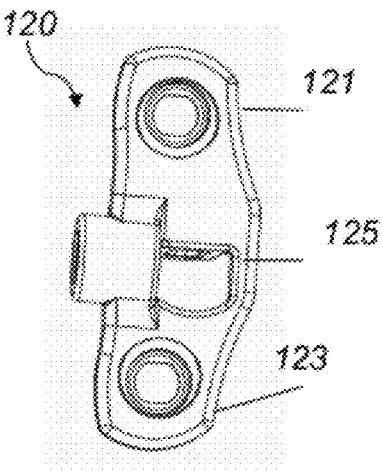
FIG.4E          FIG.4F
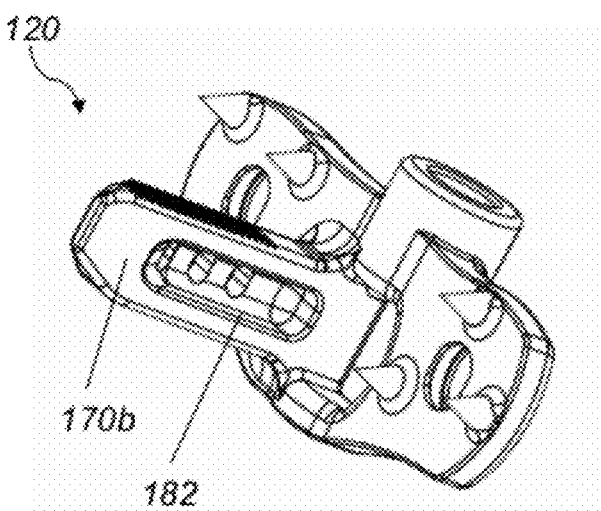
FIG.4G

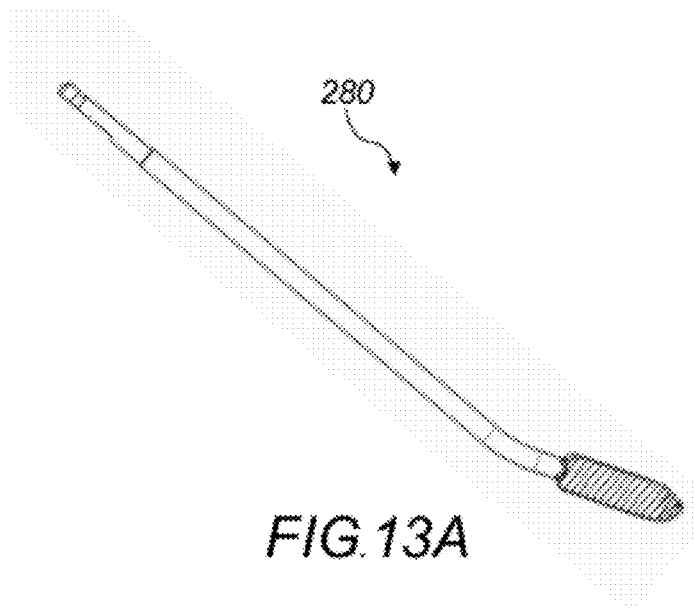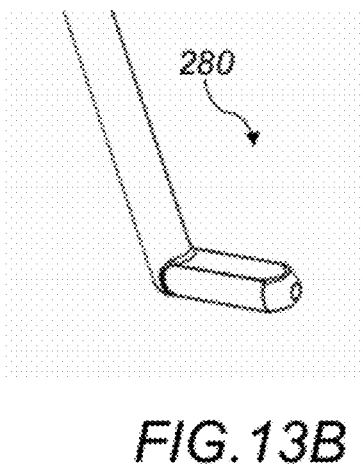
FIG.13A FIG.13B
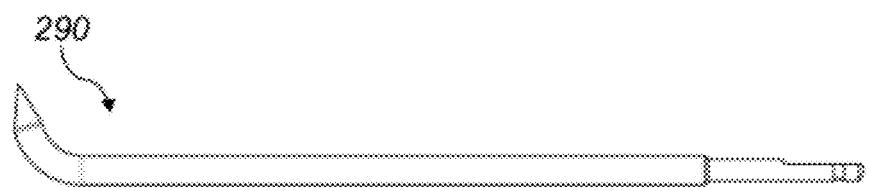
FIG.14
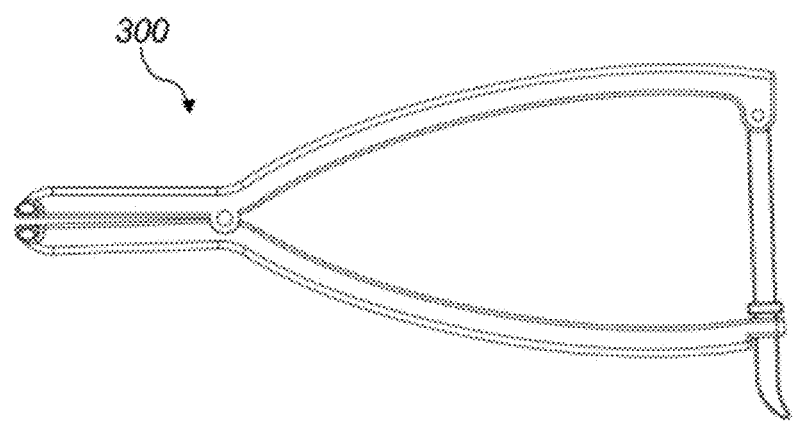
FIG.15

INTERSPINOUS SPACER IMPLANT

CROSS REFERENCE TO RELATED CO-PENDING APPLICATIONS

This application claims the benefit of U.S. provisional application Ser. No. 61/449,274 filed Mar. 4, 2011 and entitled "INTERSPINOUS SPACER IMPLANT", the contents of which are expressly incorporated herein by reference.

This application is also a continuation in part of U.S. application Ser. No. 13/182,525 filed Jul. 14, 2011 "INTERSPINOUS FIXATION IMPLANT", the contents of which are expressly incorporated herein by reference.

FIELD OF THE INVENTION

The present invention relates to an interspinous spacer implant, and more particularly, to an interspinous spacer implant that is inserted between the spinous processes of adjacent vertebrae from two different directions.

BACKGROUND OF THE INVENTION

The human spine is comprised of individual vertebrae 30 that are connected to each other to form a spinal column 29, shown in FIG. 1A. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column 29. The neural arches 36 are positioned so that the space they enclose forms a tube, i.e., the spinal canal 37. The spinal canal 37 houses and protects the spinal cord and other neural elements. A fluid-filled protective membrane, the dura 38, covers the contents of the spinal canal. The spinal column is flexible enough to allow the body to twist and bend, but sturdy enough to support and protect the spinal cord and the other neural elements. The vertebrae 30 are separated and cushioned by thin pads of tough, resilient fiber known as inter-vertebral discs 40. Disorders of the spine occur when one or more of the individual vertebrae 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relieve the patient of discomfort.

Several spinal fixation systems exist for stabilizing the spine so that bony fusion is achieved. The majority of these fixation systems utilize rods that attach to screws threaded into the vertebral bodies or the pedicles 48, shown in FIG. 1C. In some cases component fixation systems are also used to fuse two adjacent vertebral segments. The component fixation systems usually include two longitudinal components that are each placed laterally to connect two adjacent pedicles of the segments to be fused. The longitudinal components may be plates, rods, and wires, among others. This system can be extended along the sides of the spine by connecting two adjacent pedicles at a time, similar to the concept of a bicycle chain. Current component fixation systems are designed to function in place of rods with the advantage of allowing intersegmental fixation without the need to contour a long rod across multiple segments. Both the component systems and the rod systems add bulk along the lateral aspect of the spine and limit access to the pars and transverse processes for decortication and placement of bone graft. In order to avoid this limitation, many surgeons decorticate before placing the rods. However, decortication is not always desirable because it increases the amount of blood loss and makes it more difficult to maintain a clear operative field. Placing rods or components lateral to the spine leaves the center of the spinal canal that contains the dura, spinal cords and nerves completely exposed. In situations where problems develop at the junction above or below the fused segments additional fusion may be necessary. However, the rod fixation system is difficult to extend to higher or lower levels that need to be fused. Although there are connectors and techniques to lengthen the fixation via rods, they tend to be complex, difficult to use, and time consuming.

It is desirable to have a spinal stabilization device that does not add bulk to the lateral aspect of the spine, is extendable, and does not limit access to the pars and transverse processes for decortication and placement of bone graft.

SUMMARY OF THE INVENTION

In general, in one aspect, the invention features an implantable assembly for stabilization of two adjacent spinous processes in a spinal column. The assembly includes an elongated first component, an elongated second component, a hub spacer, an interspinous spacer, and first and second locking screws. The elongated first component extends along a first axis and is configured to be placed to the left side of the two adjacent spinous processes. The elongated second component extends along a second axis and is configured to be placed to the right side of the two adjacent spinous processes. The first and second components are arranged opposite and parallel to each other. The hub spacer is configured to be placed between the first and second spinous processes transversely to the first and second components. The interspinous spacer is configured to be inserted transversely through the interspinous ligament from left to right direction relative to the first component or from right to left direction relative to the second component or from the front of the interspinous ligament. The interspinous spacer is shaped and dimensioned to be placed behind the first and second components, behind the hub spacer, and between the first and second spinous processes. The first and second locking screws secure the first and second components onto the first and second spinous processes, respectively.

Implementations of this aspect of the invention may include one or more of the following features. The interspinous spacer comprises an elongated body having front and back surfaces, top and bottom surfaces and left and right surfaces and the top and bottom surfaces comprise central recesses shaped and dimensioned to receive the first and second spinous processes, respectively. The front portions of the top and bottom surfaces of the interspinous spacer are angled and the right surface is multifaceted. The back surface of the interspinous spacer is convexly curved. The front surface of the interspinous spacer comprises an elongated recess extending the length of the interspinous spacer. The interspinous spacer further comprises two openings extending from the front surface to the back surface of the interspinous spacer and the two openings are shaped and dimensioned to receive prongs of an insertion tool. The assembly further includes an interspinous spacer insertion tool and the insertion tool comprises an elongated rod terminating into first and second prongs, an axially movable sleeve surrounding the elongated rod, a rotationally movable knob configured to trigger the axial motion of the sleeve and a removable handle. The first and second prongs are configured to engage first and second openings in the interspinous spacer and moving the sleeve down compresses the two prongs together and locks the inserter tool onto the interspinous spacer. The first and second openings are located on the front surface of the interspinous spacer. Alternatively, the first opening is located on the front surface of the interspinous spacer and the second opening is located on the left side surface of the interspinous spacer. The first component comprises a first elongated body and a first integral post, and the second component comprises a second elongated body and a second integral post. The first and second integral posts interface with each and form the hub spacer. Each of the first and second elongated bodies comprises a parallelepiped structure having parallel front and back surfaces, parallel left and right surfaces, and parallel top and bottom surfaces. The back surfaces of the first and second elongated bodies are convexly curved so that a middle portion of each of the first and second elongated bodies protrudes relative to the top and bottom portions of each of the first and second elongated bodies, respectively. The first elongated body further comprises a first through-opening in the middle portion and the first through-opening extends from the left surface to the right surface and comprises a first cross section. The second elongated body further comprises a first through-opening in the middle portion and the first through-opening extends from the left surface to the right surface and comprises a second cross section. The first integral post extends from the middle portion, perpendicularly to the right side surface of the first elongated body and comprises a hollow body. The hollow body is adjacent to the first through-opening and is oriented so that the hollow body's cross section matches the second cross of the first through-opening of the second elongated body. The second integral post extends from the middle portion, perpendicularly to the left side surface of the second elongated body and comprises a hollow body, and the hollow body is adjacent to the first through-opening and is oriented so that the body's cross section matches the first cross section of the first through-opening of the first elongated body. Each of the first and second elongated bodies further comprises a cylindrical projection extending from the middle portion perpendicular to the front surface and wherein the cylindrical projection comprises a second through-opening extending from the front to the back surface of each of the first and second elongated bodies, and the second through-opening intersects the first through-opening perpendicularly. Each of the top portions of the first and second elongated bodies comprises one or more teeth protruding from the top right surface of the first elongated body and the top left surface of the second elongated body, respectively, and each of the bottom portions of the first and second elongated bodies comprises one or more teeth protruding from the bottom right surface of the first elongated body and the bottom left surface of the second elongated body, respectively. The assembly further includes first and second set-screws dimensioned to fit within the second through-openings of the first and second elongated bodies, respectively, and to secure the second and first integral posts within the first through-openings in the first and second elongated bodies, respectively. The assembly further includes graft material placed within the hub spacer. The first elongated body further comprises third and fourth through-openings formed in the top and bottom portions of the first elongated body and the third and fourth through-openings extend from the left to the right surfaces of the first elongated body and are shaped and dimensioned to receive the locking screws. The second elongated body further comprises third and fourth through-openings formed in the top and bottom portions of the second elongated body, and the third and fourth through-openings extend from the left to the right surfaces of the second elongated body and are shaped and dimensioned to receive the locking screws.

In general, in another aspect, the invention features an interspinous spacer shaped and dimensioned to be placed between first and second adjacent spinous processes. The interspinous spacer comprises an elongated body having front and back surfaces, top and bottom surfaces and left and right surfaces. The top and bottom surfaces comprise central recesses shaped and dimensioned to receive the first and second spinous processes, respectively. The interspinous spacer is configured to be inserted transversely through the interspinous ligament from left to right direction relative to the spinal axis or from right to left direction relative to the spinal axis or from the front of the interspinous ligament.

In general, in another aspect, the invention features a method for stabilizing first and second spinous processes of adjacent first and second vertebras in a spinal column. The method includes providing an implantable stabilization assembly comprising an elongated first component extending along a first axis, an elongated second component extending along a second axis, a hub spacer, an interspinous spacer, first and second locking screws and an interspinous spacer inserter tool. Next, forming an opening in the interspinous ligament between the first and second adjacent spinous processes and then distracting the first and second adjacent spinous processes. Next, attaching the interspinous spacer to the insertion tool and inserting the interspinous spacer into the opening between the first and second spinous processes either transversely from left to right direction or from the front of the opening. Next, arranging the first and second components opposite and parallel to each other and in contact with the first and second spinous process of adjacent first and second vertebras, respectively, and in front of the interspinous spacer. Next, inserting the hub spacer into the opening in front of the interspinous spacer and then securing the first and second elongated components onto the first and second spinous processes, respectively, with the locking screws.

Among the advantages of this invention may be one or more of the following. The assembly stabilizes vertebrae by attaching components to the spinous processes of the vertebrae. This stabilization device does not add bulk to the lateral aspect of the spine and does not limit access to the pars and transverse processes for decortication and placement of bone graft. The compact form of the implant assembly allows it to be implanted via mini-open surgery. The device's shape conforms to the local vertebral anatomy. In particular, the adjustable plates and spacers fit to the spinous process contour. The device may be used alone or as and adjunct to facet or pedicle screw systems. It provides multi-level (i.e., multi-vertebra) fusion through replication of the basic unit. The device is securely attached to the spinous processes via the center post, individual components, and pins. The allograft spacer promotes bone growth. The interspinous spacer may be inserted laterally from the side or from the front.

The details of one or more embodiments of the invention are set forth in the accompanying drawings and description below. Other features, objects, and advantages of the invention will be apparent from the following description of the preferred embodiments, the drawings, and the claims.

BRIEF DESCRIPTION OF THE DRAWINGS

Referring to the figures, wherein like numerals represent like parts throughout the several views:

FIG. 4E is a perspective front view of the second component of another embodiment of the interspinous fixation implant;

FIG. 4F is a side view of the second component of the embodiment of the interspinous fixation implant of FIG. 4E;

FIG. 4G is a bottom perspective view of the second component of the embodiment of the interspinous fixation implant of FIG. 4E;

FIG. 13A is a schematic view of flat rasp tool;

FIG. 13B is a schematic view of a round rasp tool;

FIG. 14 is a schematic view of a hooked dilator;

FIG. 15 is a schematic view of a hub sizer tool;

DETAILED DESCRIPTION OF THE INVENTION

Figure 1A:
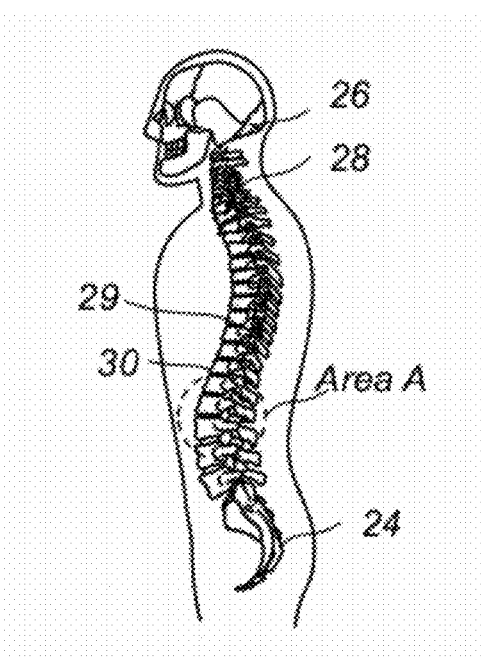
FIG. 1A is a side view of the human spinal column.
Figure 1B:
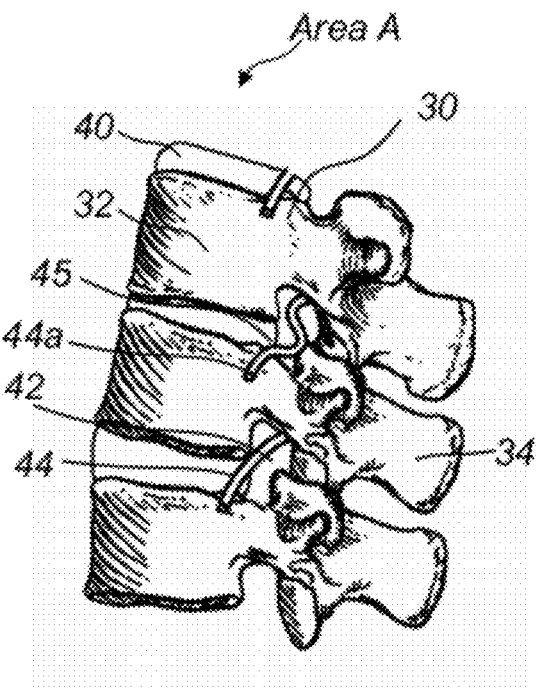
FIG. 1B is an enlarged view of area A of FIG. 1A.
Figure 1C:
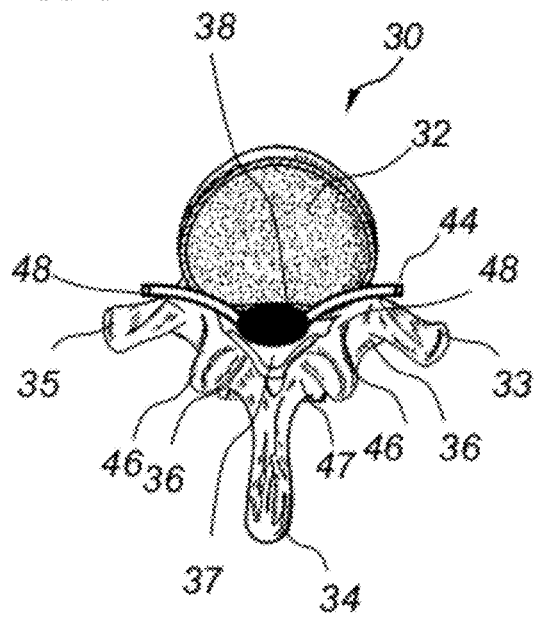
FIG. 1C is an axial cross-sectional view of a lumbar vertebra.
Figure 2:
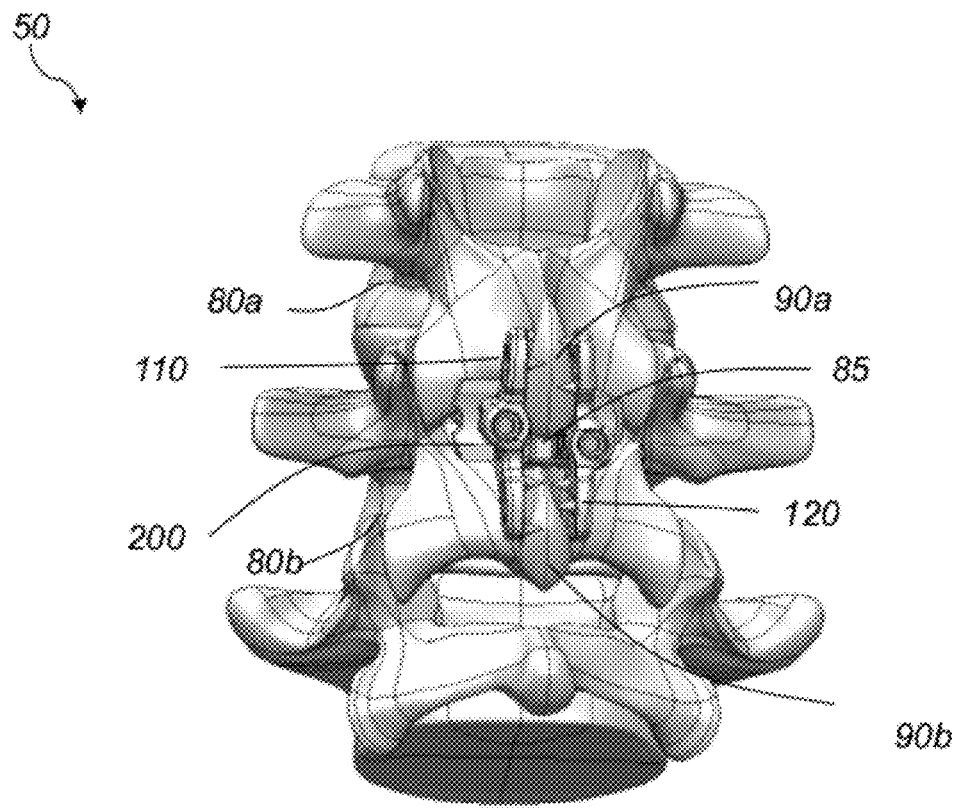
FIG. 2 is a perspective view of the interspinous fixation implant assembly of this invention, used to secure two adjacent vertebrae.
Figure 3:
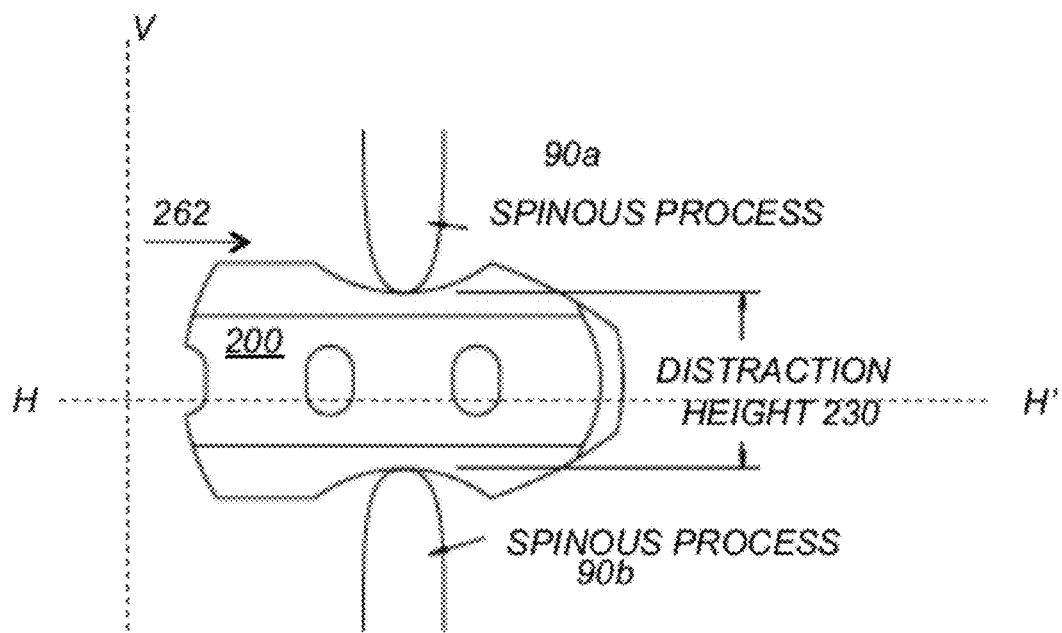
FIG. 3 is a schematic view of the interspinous spacer implant of the interspinous fixation implant assembly of FIG. 2.

The present invention relates to a system and a method for an improved spinous process fixation implant assembly 50, shown in FIG. 2. The spinous process fixation implant assembly 50 includes a spinous process fixation implant 100 and an interspinous spacer implant 200. The spinous process fixation implant 100 includes elongated first and second components 110, 120, that are arranged opposite and parallel to each other. First and second spinous processes 90a, 90b of first and second adjacent vertebrae 80a, 80b are clamped between the first and second components 110, 120, respectively, and are separated by the interspinous spacer implant 200, as shown in FIG. 2 and FIG. 3.

Figure 4A:
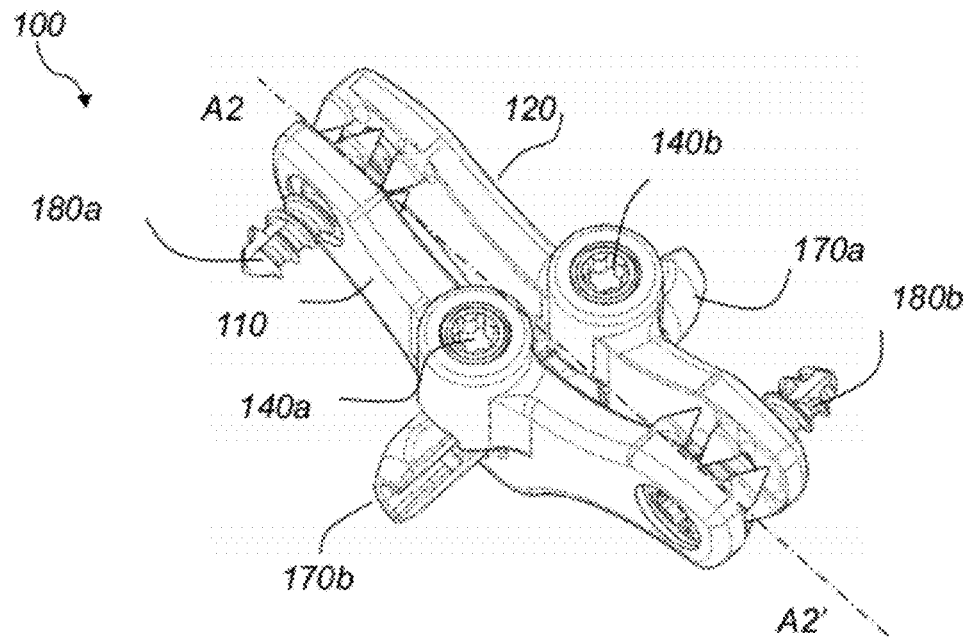
FIG. 4A is a perspective view of the interspinous fixation implant of FIG. 2.
Figure 4B:
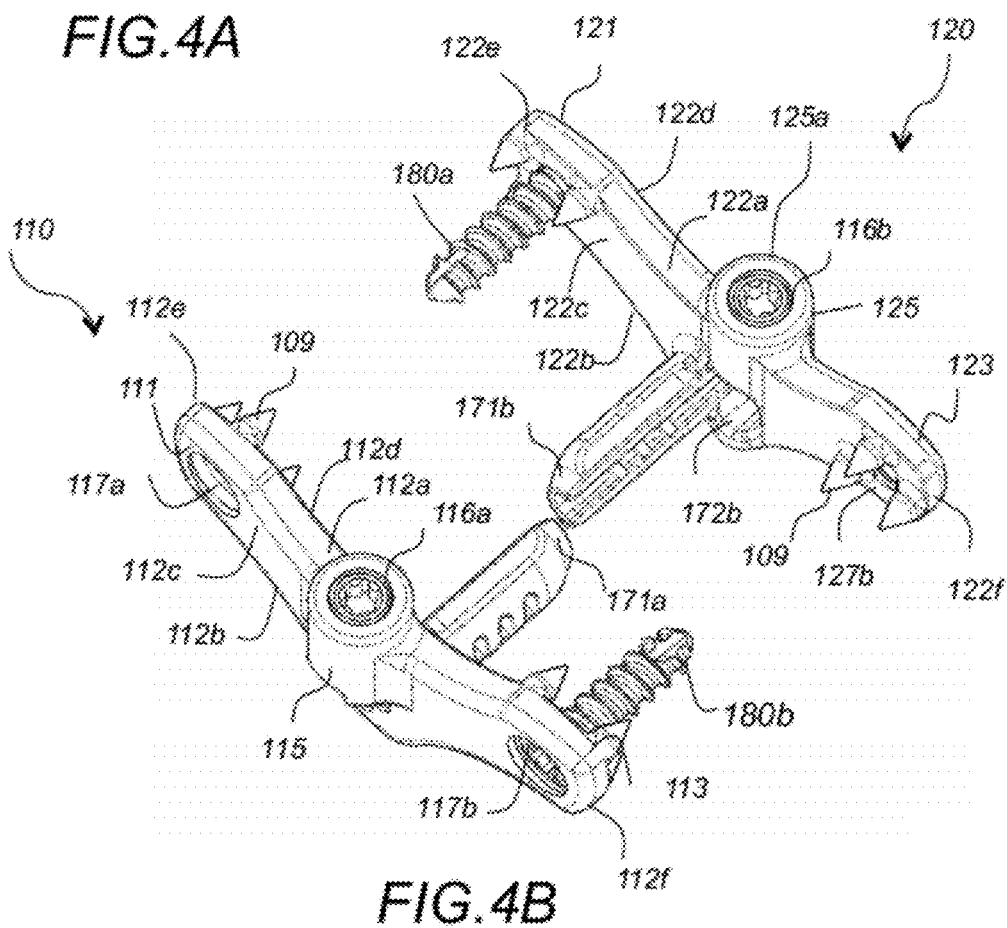
FIG. 4B is a is a partially exploded view of the interspinous fixation implant of FIG. 4A.
Figure 4C:
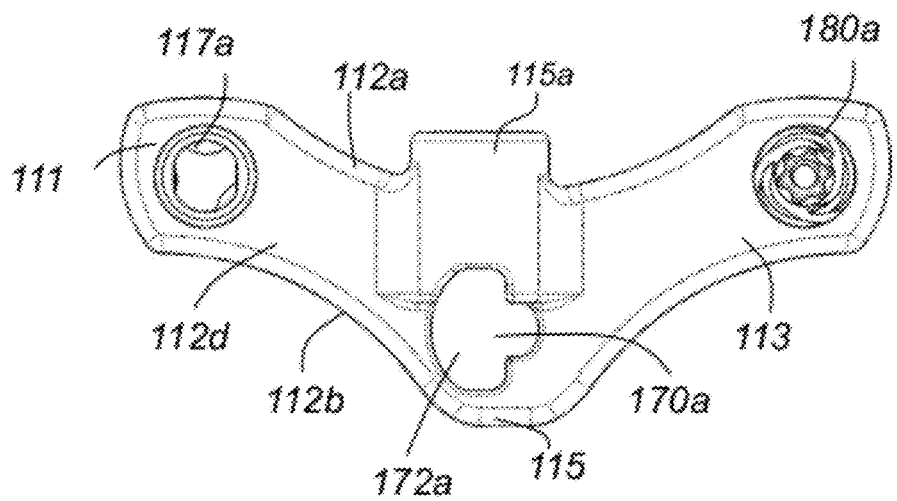
FIG. 4C is a side view of the first component of the interspinous fixation implant of FIG. 4A.

Referring to FIG. 4A-4C, spinous process fixation implant 100 includes first elongated component 110, second elongated component 120, top and bottom pins, 180a, 180b, and set screws 140a, 140b. First component 110 includes an elongated body 112 and one integral post 170a. Elongated body 112 has an essentially parallelepiped structure having parallel front and back surfaces 112a, 112b, parallel left and right side surfaces 112c, 112d and parallel top and bottom surfaces 112e, 112f, respectively. Elongated body 112 is convexly curved so that its top and bottom portions 111, 113 protrude forward relative to its middle portion 115, as shown in FIG. 4C. Middle portion 115 includes an opening 172a extending from the left surface 112c to the right surface 112d. Top portion 111 includes teeth 109 protruding from the top of right surface 112d. Bottom portion 113 also includes teeth 109 protruding from the bottom of right surface 112d. Opening 172a has a semi-circular cross-section and is dimensioned to be slightly larger than or equal to the dimensions of post 170b of component 120, so that post 170b can pass through it. Middle portion 115 also includes a cylindrical projection 115a having an opening 116a extending from the top surface 112a to the back surface 112b. Opening 116a receives set screw 140a and has dimensions matching the dimensions of screw 140a. Screw 140a secures the position of post 170b of the second component 120 onto post 170a of the first component 110 within opening 172a. Post 170a is integral with component 110 and has an essentially hollow semi-cylindrical structure. Post 170a extends perpendicularly to the right side surface 112d of the elongated body 112 from its middle portion 115. Post 170a is adjacent to opening 172a and is oriented so that its cross-section forms a full circle together with the semi-circular opening 172a, as shown in FIG. 4C.

Referring to FIG. 4B, second component 120 is the same as the first component 110 and is rotated 180 degrees relative to the orientation of the first component 110. Second component 120 includes an elongated body 122 and one integral post 170b. Elongated body 122 has an essentially parallelepiped structure having parallel front and back surfaces 122a, 122b, parallel left and right side surfaces 122c, 122d and parallel top and bottom surfaces 122e, 122f, respectively. Elongated body 122 is also convexly curved so that its top and bottom portions 121, 123 protrude forward relative to its middle portion 125. Middle portion 125 includes an opening 172b extending from the left surface 122c to the right surface 122d. Top portion 121 includes teeth 109 protruding from the top of right surface 122d. Bottom portion 123 also includes teeth 109 protruding from the bottom of right surface 122d. Opening 172b has a semi-circular cross-section and is dimensioned to be slightly larger than or equal to the dimensions of post 170a of component 110, so that post 170a can pass through it. Middle portion 125 also includes a cylindrical projection 125a having an opening 116b extending from the top surface 122a to the back surface 122b. Opening 116b receives set screw 140b and has dimensions matching the dimensions of screw 140a. Screw 140a secures the position of post 170a of the first component 110 onto post 170*b* of the second component 120 within opening 172*b*. Post 170*b* is integral with component 120 and has an essentially hollow semi-cylindrical structure 182, shown in FIG. 4G. Post 170*b* extends perpendicularly to the right side surface 122*d* of the elongated body 122 from its middle portion 125. Post 170*b* is adjacent to opening 172*b* and is oriented so that its cross-section forms a full circle together with the semi-circular opening 172*b*. Posts 170*a*, 170*b* have tapered front ends 171*a*, 171*b*. Tapered front ends 171*a*, 171*b*, help the insertion of the posts 170*a*, 170*b* through the interspinous area 85 and the openings 172*b*, 172*a*, respectively. In another embodiment, elongated body 122 of component 120 is not curved, and the top and bottom portions 121, 123 do not protrude relative to the middle portion 125, as shown in FIG. 4F and FIG. 4E. Similarly, elongated body 112 of component 110 is not curved. In this embodiment, the front ends 171*a*, 171*b* of posts 170*a*, 170*b* are closed off and chamfered, as shown in FIG. 4E.

Figure 5:
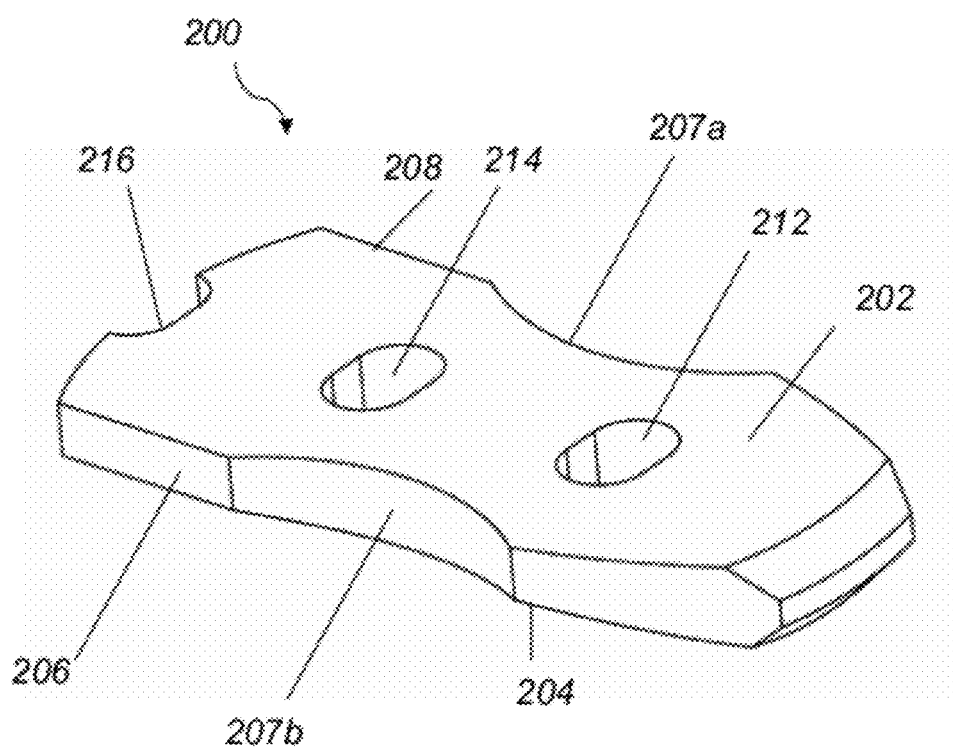
FIG. 5 is a perspective view of the interspinous spacer implant of FIG. 3.
Figure 6:
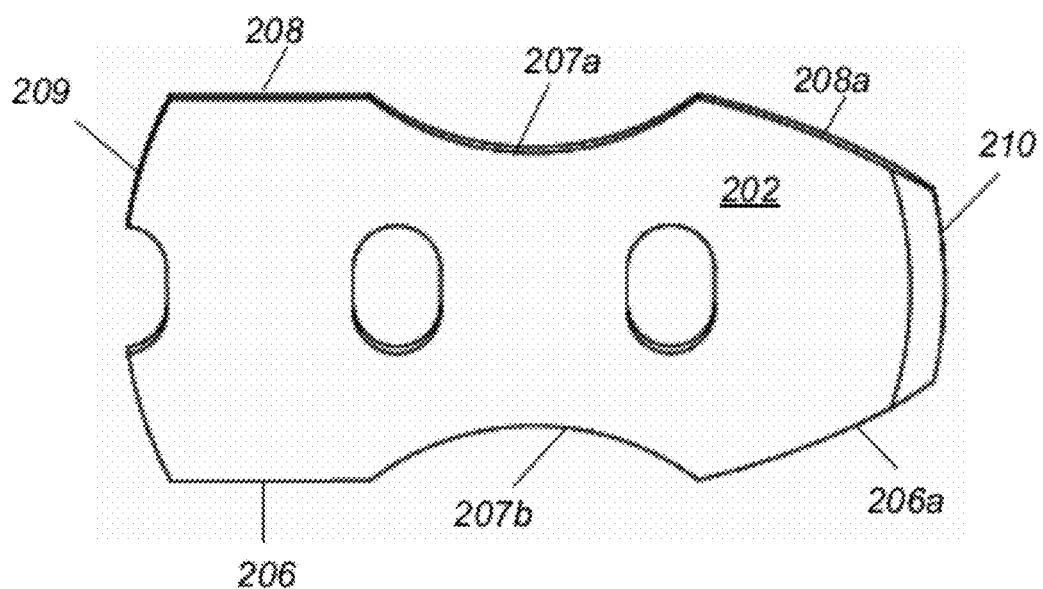
FIG. 6 is a front view of the interspinous spacer implant of FIG. 5.
Figure 7:
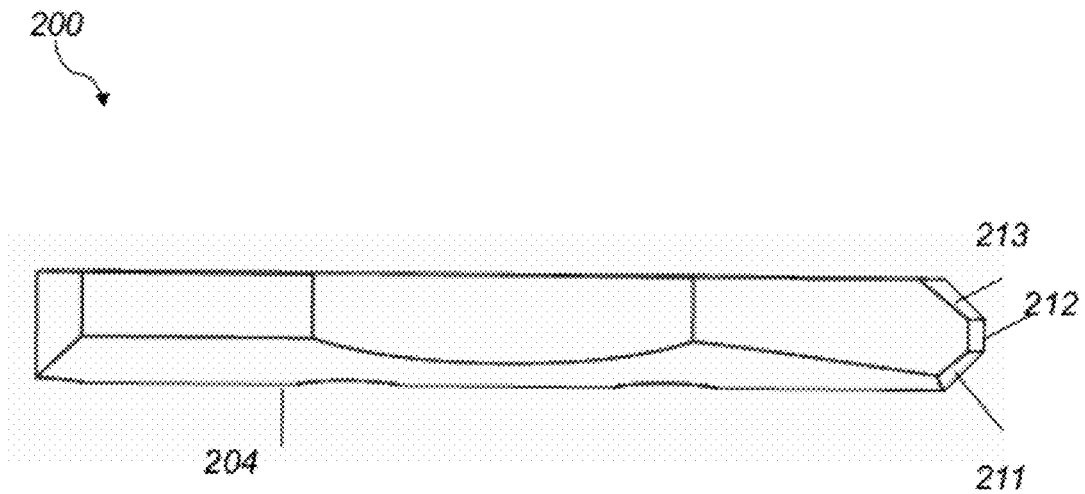
FIG. 7 is a top view of the interspinous spacer implant of FIG. 5.
Figure 8:
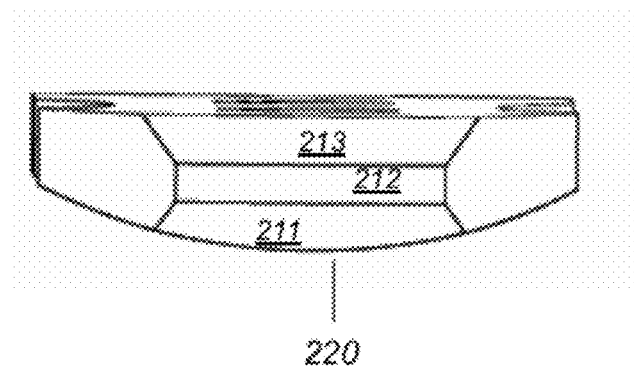
FIG. 8 is a side view of the interspinous spacer implant of FIG. 5.
Figure 9A:
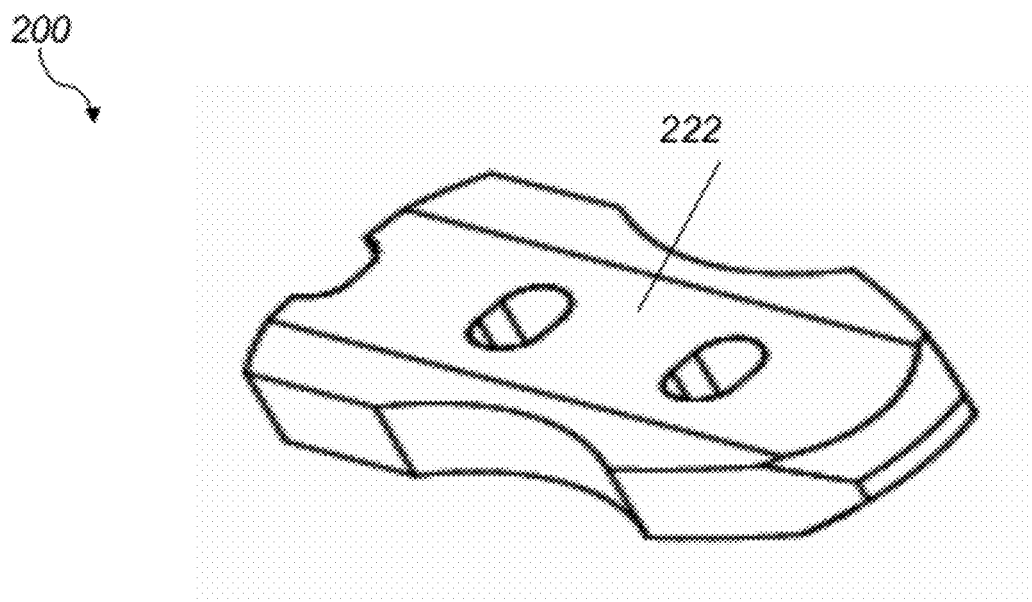
FIG. 9A is a perspective view of another embodiment of the interspinous spacer implant.
Figure 9B:
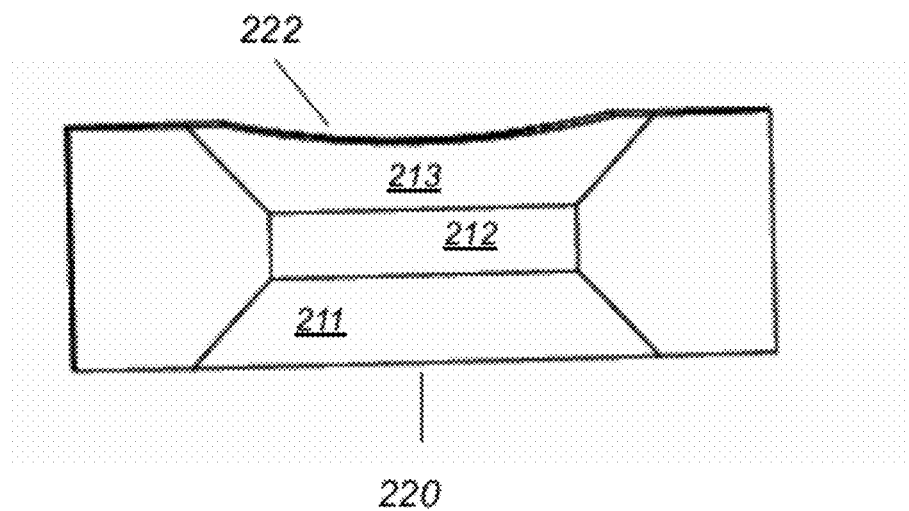
FIG. 9B is a side view of the interspinous spacer implant of FIG. 9A.

Referring to FIG. 5 and FIG. 6, interspinous spacer implant 200 includes an elongated body having a front surface 202, back surface 204, bottom surface 206, top surface 208, left side surface 209 and right side surface 210. Implant 200 also includes openings 212, 214 and 216 extending from the front surface 202 to the back surface 204. Top and bottom surfaces 206, 208 also include central recesses 207*a*, 207*b*, respectively. Central recesses 207*a*, 207*b* are dimensioned to receive the upper the lower spinous processes 90*a*, 90*b*, respectively, as shown in FIG. 3. The front portions of top and bottom surfaces 206*a*, 208*a* are angled, thereby resulting in a narrow right side surface 210. Right side surface 210 is multifaceted and includes surfaces 211, 212, 213, shown in FIG. 7 and FIG. 8. Back surface 204 is convexly curved 220, as shown in FIG. 8. In some embodiments, the front surface 202 includes an elongated recess 222 extending the length of the implant, as shown in FIG. 9A. In this embodiment, the back surface 220 is flat, as shown in FIG. 9B. In one example, interspinous spacer implant 200 is made of bone and has a length of 30 mm, thickness in the center 3.5 mm, thickness at the sides 2.75 mm and a width of 10 mm. The width of the implant varies between 8 mm to 20 mm depending upon the distance between the adjacent spinous processes 90*a*, 90*b*.

Figures 10A, 10B, 10C:
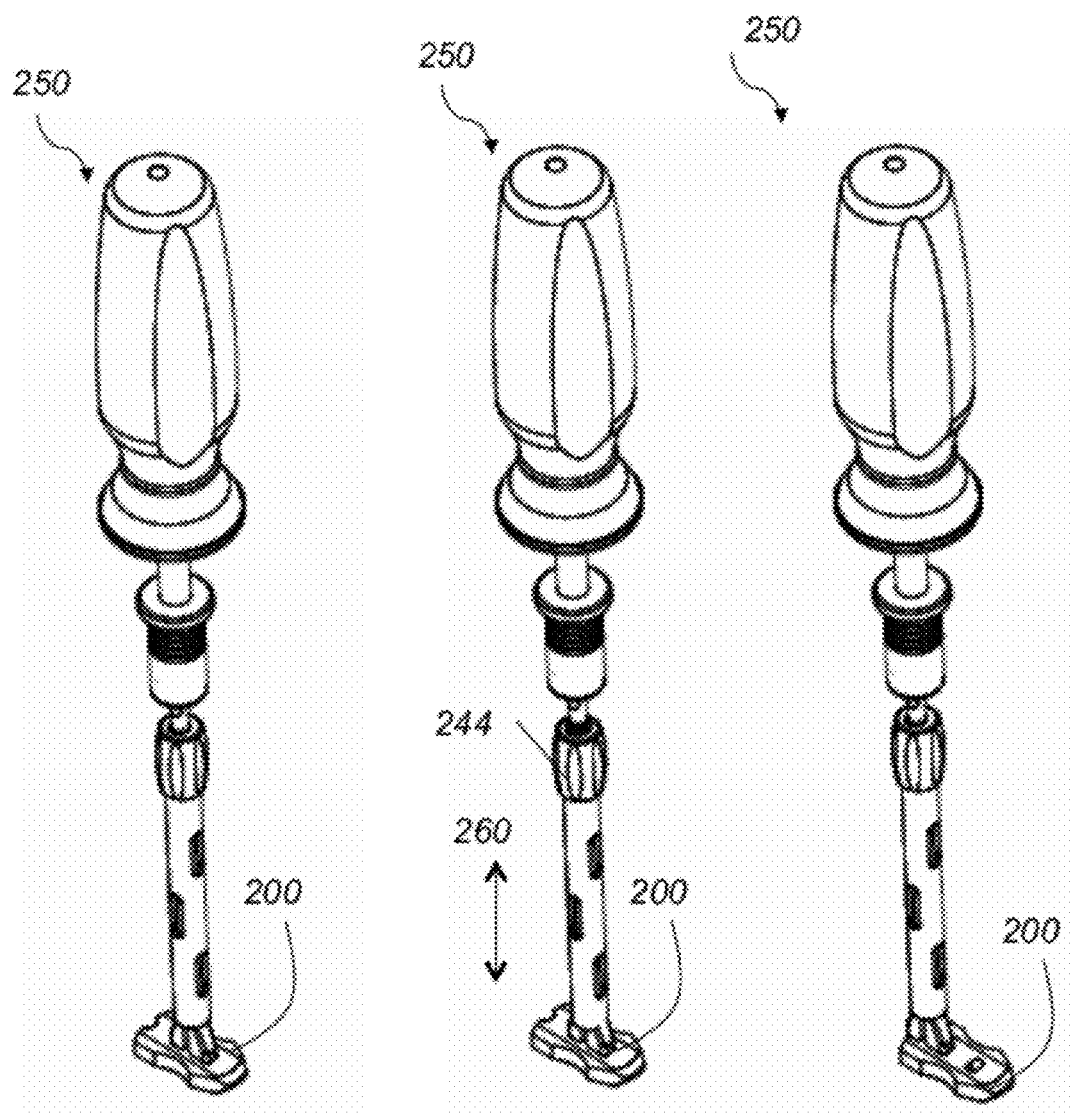
FIG. 10A is a perspective view of a spacer insertion tool used to insert the interspinous spacer implant from the front.
FIG. 10B is a perspective view of the spacer insertion tool of FIG. 10A in the secured position.
FIG. 10C is a perspective view of a spacer insertion tool used to insert the interspinous spacer implant from the side.
Figure 11:
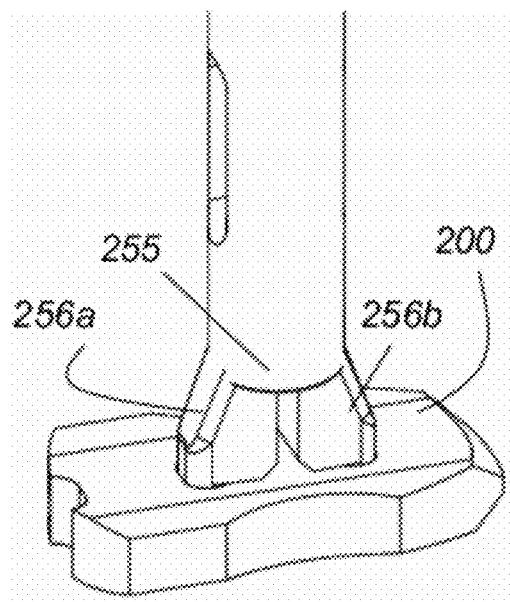
FIG. 11 is a detailed view of the end effector of the spacer insertion tool used to insert the interspinous spacer implant from the front.
Figure 12:
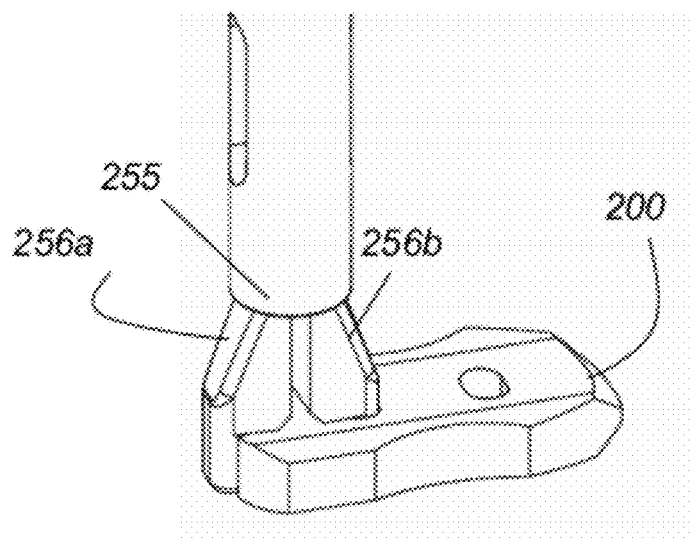
FIG. 12 is a detailed view of the end effector of the spacer insertion tool used to insert the interspinous spacer implant from the side.
Figure 16:
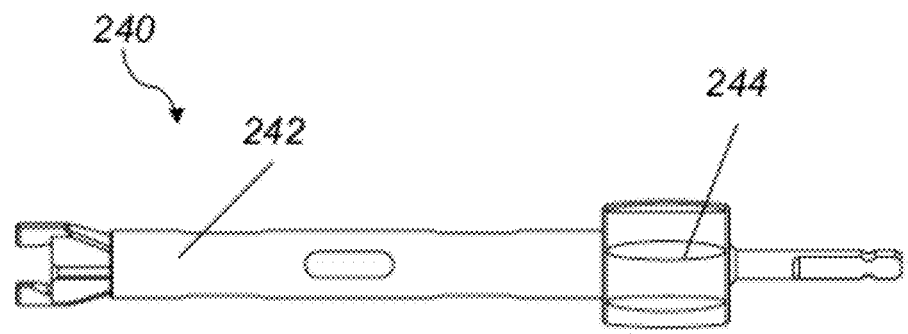
FIG. 16 is a schematic view of the inserter tool.
Figure 17:
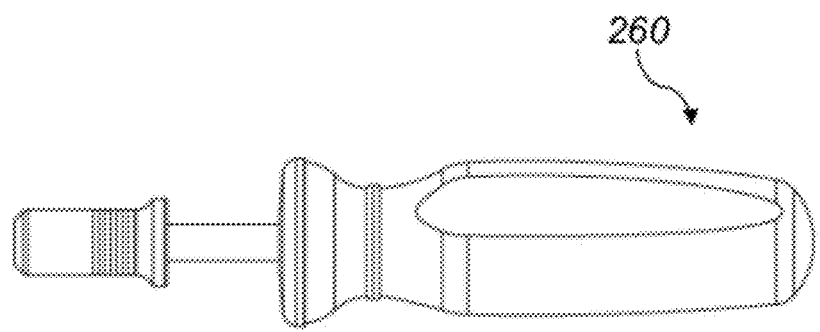
FIG. 17 is a schematic view of a handle used in connection with the inserter tool of FIG. 16.

The surgical technique for spinal stabilization using the spinous process fixation implant assembly 50 of FIG. 2 includes the following steps. First the allograft interspinous fusion spacer 200 is reconstituted by soaking in a saline solution. Next, a hooked dilator 290, shown in FIG. 14, is used to punch an opening through the anterior region of the interspinous ligament. The opening needs to be large enough to be able to accommodate both the spacer 200 and posts 170*a*, 170*b* of the fixation implant 100. Next, a distractor 300, shown in FIG. 15, is inserted into the opening and is used to spread the spinous processes 90*a*, 90*b* apart. The spinous processes 90*a*, 90*b* are spread apart and the distraction height 230 is measured. The measured distraction height 230 is used to determine the width of the spacer implant. The distractor 300 has a sliding collar on a bar at the top of the instrument that indicates the width and which standard spacer implant to use. Distraction height 230 can also be determined by using various sized round rasps ranging from 8-20 mm, shown in FIG. 13B. The measurement indicated on the distractor equals the center vertical width at the waist of the spacer. Next, the lamina, spinous processes and anterior portions around the prepared opening are roughened up using the flat or round rasp 280, shown in FIG. 13A and FIG. 13B, respectively. Next, the spacer 200 is attached to the inserter 250, shown in FIG. 10A and FIG. 10C. Inserter 250 includes the inserter component 240, shown in FIG. 16 and removable handle 260, shown in FIG. 17. There are two ways to insert the spacer 200: front-back insertion and lateral insertion. For the front-back insertion the interspinous ligament needs to be removed first. The two prongs 256*a*, 256*b* of the inserter end effector 255 are inserted in openings 212, 214 of spacer 200, as shown in FIG. 11 and FIG. 10A, and the inserter sleeve 242 is moved down along direction 260, shown in FIG. 10B, to lock the spacer 200 onto the inserter end effector 255. Inserter sleeve 242 is moved down along direction 260 by rotating the knob 244 clockwise below the handle 260. Moving the sleeve 242 down compresses the two prongs 256*a*, 256*b* together and thereby creates a secure connection between the spacer 200 and the inserter 250. The spacer 200 is inserted from the front perpendicular to directions H-H' and V-V' in the prepared opening between the spinous processes, shown in FIG. 3. The spacer 200 is oriented at approximately 45 degrees angle relative to the opening and is inserted until the waist 207*a* is between the spinous processes 90*a*, 90*b* and the midpoint of the spacer is in the interspinous space 85. Next, the inserter 250 is turned 45 degrees in the cephalad direction to place the spacer in the preferred position and to secure it in place. Once the spacer is placed in the desired position, the knob 244 is turned counter-clockwise to loosen the prongs 256*a*, 256*b*, to gradually raise the sleeve 242 and then to remove the inserter prongs 256*a*, 256*b* from the spacer 200.

For lateral insertion of the spacer 200 along direction 262, shown in FIG. 3, one prong 256*a* is inserted in the outer notch 216 and the other 256*b* is inserted in the adjacent opening 214. The center of the inserter 250 is at the side opposite the chamfered side 210 of the spacer 200. For lateral insertion, the inserter 250 may be oriented either horizontally along H-H' or vertically along VV', shown in FIG. 3. In either case the spacer 200 is inserted from the side along direction 262. The spacer 200 may be used to distract the spinous processes 90*a*, 90*b* by up to 2 mm in each direction before the center of the spacer is in the preferred location.

Figure 4D:
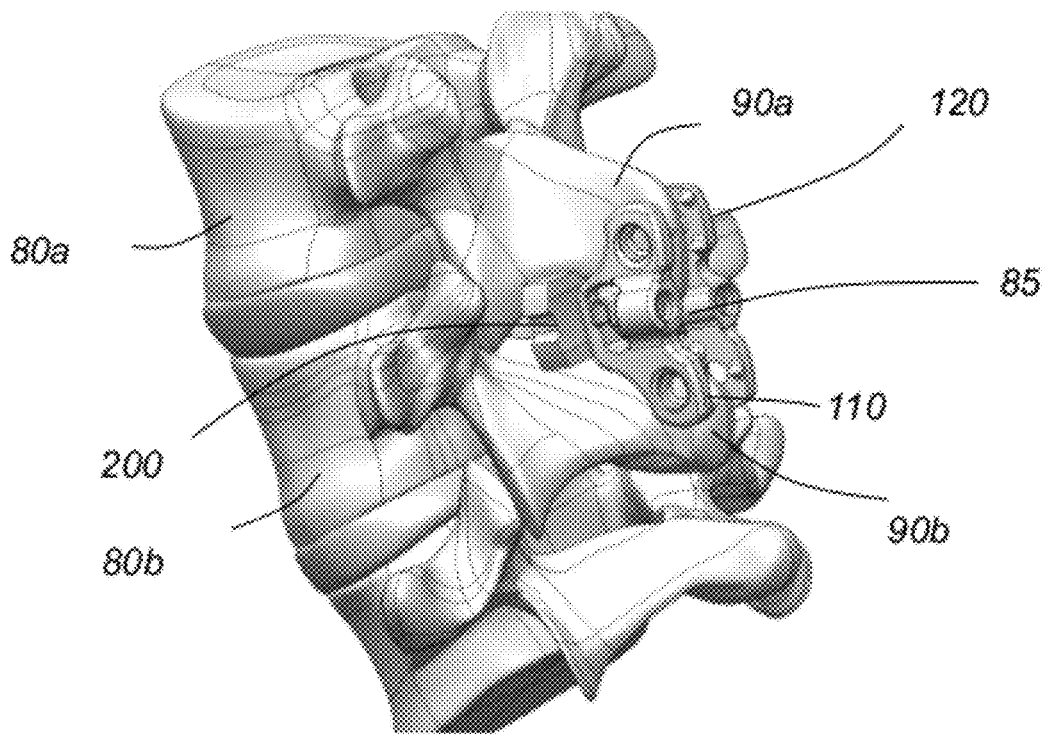
FIG. 4D is perspective side view of the interspinous fixation implant assembly of FIG. 2.

After the placement of the spacer 200, the spinous fixation implant 100 is inserted and attached to the sides of the spinous processes 90*a*, 90*b*. If the interspinous opening is large enough to accommodate both the spacer 200 and the vertical posts 170*a*, 170*b* of the spinous fixation implant 100, the same opening is used for the spacer 200 and the fixation implant 100. In cases where the interspinous opening is not large enough, a second opening is punched with the hooked dilator 290 for accommodating the fixation implant 100. The spinous processes may need to be further distracted with distractor 300 in order to accommodate the fixation implant 100. Next, the first component 110 is placed in contact with the left sides of top and bottom spinous process 90*a*, 90*b* of adjacent vertebrae 80*a*, 80*b*, respectively, as shown in FIG. 4D. Post 170*a* is placed in the second interspinous opening between the top and bottom spinous processes 90*a*, 90*b*. Next, second component 120 is placed in contact with the right sides of top and bottom spinous process 90*a*, 90*b* of adjacent vertebrae 80*a*, 80*b*, respectively. Post 170*a* of the first component 110 is inserted into opening 172*b* of the second component 120, and post 170*b* of the second component 120 is inserted into openings 172*a* of the first component 110. Fully inserted posts 170*a*, 170*b* interface with the corresponding openings 172*a*, 172*b*, and with each other to form a hollow cylindrical hub structure 124, as shown in FIG. 4A. Next, the two components 110, 120 are pressed against the left and right of the top and bottom spinous processes 90a, 90b, respectively and set screws 140a, 140b are screwed into openings 116c, 116d, to compress and secure the position of the two components 110, 120, respectively. Teeth 109 at the top and bottom portions of components 110, 120 penetrate into the sides of the top and bottom spinous processes 90a, 90b, respectively.

Several embodiments of the present invention have been described. Nevertheless, it will be understood that various modifications may be made without departing from the spirit and scope of the invention. Accordingly, other embodiments are within the scope of the following claims.

What is claimed is:

1. An interspinous spacer comprising an elongated body having front and back surfaces, top and bottom surfaces and left and right surfaces, wherein the interspinous spacer is shaped and dimensioned to be placed between first and second adjacent spinous processes and wherein the top and bottom surfaces comprise central recesses shaped and dimensioned to receive the first and second spinous processes, respectively, and wherein the interspinous spacer is configured to be inserted transversely through the interspinous ligament from left to right direction relative to the spinal axis or from right to left direction relative to the spinal axis or from the front of the interspinous ligament;
    wherein the interspinous spacer further comprises two openings extending from the front surface to the back surface of the interspinous spacer and wherein the two openings are shaped and dimensioned to receive prongs of an insertion tool; and
    wherein the interspinous spacer further comprises an interspinous spacer insertion tool and wherein said insertion tool comprises an elongated rod terminating to first and second prongs, an axially movable sleeve surrounding the elongated rod, a rotationally movable knob configured to trigger the axial motion of the sleeve and a removable handle and wherein said first and second prongs are configured to engage first and second openings in the interspinous spacer and wherein moving the sleeve down compresses the two prongs together and locks the inserter tool onto the interspinous spacer.

2. The interspinous spacer of claim 1, wherein front portions of the top and bottom surfaces of the interspinous spacer are angled, the right side surface is multifaceted and the back surface is convexly curved.

3. The interspinous spacer of claim 2, wherein the front surface of the interspinous spacer comprises an elongated recess extending the length of the interspinous spacer.

4. The interspinous spacer of claim 1, wherein the first and second openings are located on the front surface of the interspinous spacer.

5. The interspinous spacer of claim 1, wherein said first opening is located on the front surface of the interspinous spacer and said second opening is located on the left side surface of the interspinous spacer.

6. An interspinous spacer comprising an elongated body having front and back surfaces, top and bottom surfaces and left and right surfaces, wherein the interspinous spacer is shaped and dimensioned to be placed between first and second adjacent spinous processes and wherein the top and bottom surfaces comprise central recesses shaped and dimensioned to receive the first and second spinous processes, respectively, and wherein the interspinous spacer is configured to be inserted transversely through the interspinous ligament from left to right direction relative to the spinal axis or from right, to left direction relative to the spinal axis or from the front of the interspinous ligament:
    wherein front portions of the top and bottom surfaces of the interspinous spacer are angled, the right side surface is multifaceted and narrower than the left side surface;
    wherein the interspinous spacer further comprises two openings extending from the front surface to the back surface of the interspinous spacer and wherein the two openings are shaped and dimensioned to receive prongs of an insertion tool; and
    wherein the interspinous spacer further comprising an interspinous spacer insertion tool and wherein said insertion tool comprises an elongated rod terminating to first and second prongs, an axially movable sleeve surrounding the elongated rod, a rotationally movable knob configured to trigger the axial motion of the sleeve and a removable handle and wherein said first and second prongs are configured to engage first and second openings in the interspinous spacer and wherein moving the sleeve down compresses the two prongs together and locks the inserter tool onto the interspinous spacer.

\* \* \* \* \*